United States Patent [19]

Fleisch et al.

[11] Patent Number: 4,492,704

[45] Date of Patent: Jan. 8, 1985

[54] QUINOLINE QUINONES AND ANTI-ASTHMATIC USE THEREOF

[75] Inventors: Jerome H. Fleisch, Indianapolis; Winston S. Marshall, Bargersville; George J. Cullinan, Trafalgar, all of Ind.

[73] Assignee: Eli Lilly and Company, Indianapolis, Ind.

[21] Appl. No.: 430,895

[22] Filed: Sep. 30, 1982

[51] Int. Cl.$^3$ .................. A61K 31/505; A61K 31/47; C07D 215/24; C07D 401/04

[52] U.S. Cl. ............................... 424/269; 424/248.57; 544/128; 546/159

[58] Field of Search ........... 546/159; 424/269, 248.57; 544/128

[56] References Cited

PUBLICATIONS

Long et al., *J. Chem. Soc.*, 3919–3924 (1953).
Petrow et al., *J. Chem. Soc.*, 570–574 (1954).
Pratt, Y. T., *J. Org. Chem.*, 27, 3905–3910 (1962).
Pratt et al., *J. Amer. Chem. Soc.*, 77, 37–40 (1955).
Pratt et al., *J. Amer. Chem. Soc.*, 82, 1155–1161 (1960).

*Primary Examiner*—Glennon H. Hollrah
*Assistant Examiner*—D. B. Springer
*Attorney, Agent, or Firm*—Karen B. Dow; Arthur R. Whale

[57] ABSTRACT

This invention relates to a class of quinoline quinones, which are useful for the therapy of immediate hypersensitivity reactions, such as asthma, and in treating any condition characterized by excessive release of leukotrienes. This invention also includes a method for treating these conditions, which comprises administering to animals, including humans, an effective dose of the quinoline quinone compounds. A further part of this invention is pharmaceutical formulations containing these pharmacologically-active compounds.

19 Claims, No Drawings

QUINOLINE QUINONES AND ANTI-ASTHMATIC USE THEREOF

BACKGROUND OF THE INVENTION

This invention relates to a class of quinoline-5,8-quinones (also called 5,8-quinolinediones), which are useful for the therapy of immediate hypersensitivity reactions and conditions characterized by excessive release of slow-reacting substances or leukotrienes. This invention also includes a method for treating the above conditions, which comprises administering to animals, including humans, an effective dose of the quinoline quinone compounds.

Various 6-substituted-quinoline-5,8-quinones have been prepared by those skilled in the art; however, the references describing these preparations do not teach the use of the compounds as inhibitors of leukotriene release. For example, Long, R. and Schofield, K. in "Some Properties and Reactions of Quinoline-5:8-quinones", J. Chem. Soc., 3919-3924 (1953) describe the preparation of 6-substituted quinoline-5,8-quinones, in which the 6-position substituent can be: hydroxy, halo, alkyl, anilino, or hydrogen. Long and Schofield indicate that antimalarial action and bacteriostatic properties are expected, whereas the quinones taught herein are useful in treating excessive release of leukotrienes.

Antibacterial properties are described for 6-methyl and 6-anilino-quinoline-5,8-quinones in Petrow, V. and Sturgeon, B. "Some Quinoline-5:8-quinones", J. Chem. Soc., 570-574 (1954). Other substituted quinoline-5,8-quinones are described in: Pratt, Y. T. "Quinolinequinones, VI. Reactions with Aromatic Amines", J. Org. Chem., 27, 3905-3910 (1962); Pratt, Y. T. and Drake, N. L. "Quinolinequinones. II. N-Substituted 6-Amino-5,8-quinolinequinones", J. Amer. Chem. Soc., 77, 37-40 (1955); and Pratt, Y. T. and Drake, N. L. "Quinolinequinones. V. 6-Chloro- and 7-Chloro-5,8-quinolinequinones", J. Amer. Chem. Soc., 82, 1115-1161 (1960).

A copending application, Ser. No. 429,589, filed Sept. 30, 1982, describes a class of isoquinoline quinones, while another copending application, Ser. No. 430,896, also filed Sept. 30, 1982, describes a class of quinoxalinediones. Both applications teach the use of the compounds to inhibit the release of leukotrienes and to treat immediate hypersensitivity reactions, such as asthma.

SUMMARY OF THE INVENTION

According to the present invention there is provided a compound of formula (I):

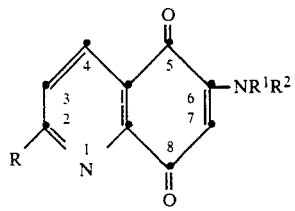

wherein
R is hydrogen or $C_1$-$C_3$ alkyl;
$R^1$ and $R^2$ are hydrogen; $C_3$-$C_6$ cycloalkyl; $C_2$-$C_6$ alkenyl; tetrahydronaphthyl; together with the nitrogen atom form a morpholine ring; or phenyl substituted by $R^3$; and $R^3$ is hydrogen; $C_1$-$C_6$ alkyl, except ortho ethyl, and para methyl; $C_2$-$C_6$ alkenyl; $C_1$-$C_6$ alkoxy; halo, except para chloro; trifluoromethyl, except in the para position; nitro; hydroxy; $C_1$-$C_3$ alkylthio; or $C_1$-$C_3$ alkylcarbonyl;

providing that $R^1$ and $R^2$ are not both hydrogen or phenyl and further providing that $R^1$ is not phenyl when R and $R^2$ are hydrogen.

A method of treating any condition characterized by the excessive release of leukotrienes and a method of treating immediate hypersensitivity reactions, such as asthma, are also described. Further provided by this invention are formulations for these pharmaceutically-active compounds.

DETAILED DESCRIPTION OF THE INVENTION

In addition to the compounds of formula I, this invention also provides a method of treating an animal, including a human, suffering from or susceptible to any condition characterized by an excessive release of leukotrienes, which comprises administering to said animal a therapeutically-effective amount of a compound of formula (II):

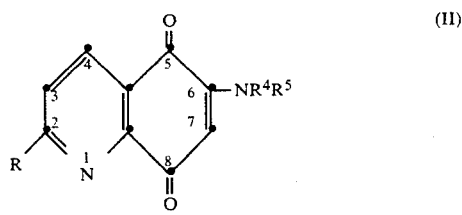

wherein
R is hydrogen or $C_1$-$C_3$ alkyl;
$R^4$ and $R^5$ are hydrogen; $C_1$-$C_6$ alkyl; $C_3$-$C_6$ cycloalkyl; $C_2$-$C_6$ alkenyl; $C_1$-$C_6$ alkylamino; tetrahydronaphthyl; together with the nitrogen atom form a morpholine or piperidine ring; or phenyl substituted by $R^3$; and
$R^3$ is hydrogen; $C_1$-$C_6$ alkyl, except ortho ethyl; $C_2$-$C_6$ alkenyl; $C_1$-$C_6$ alkoxy; halo; trifluoromethyl, except in the para position; nitro; hydroxy; $C_1$-$C_3$ alkylthio; or $C_1$-$C_3$ alkylcarbonyl.

Also provided is a method of treating an animal, including a human, suffering from or susceptible to an immediate hypersensitivity reaction of the type represented by asthma, which comprises administering to said animal a therapeutically-effective amount of a compound of formula (II) as defined above.

According to a further aspect of the present invention there is provided a pharmaceutical formulation which comprises as the active ingredient a therapeutically-effective amount of a compound of formula (I) as defined above, associated with a pharmaceutically-acceptable carrier therefor.

Preferred compounds are those wherein $R^1$ or $R^4$ is phenyl or substituted phenyl and $R^2$ or $R^5$ is hydrogen. Even more preferred are: 6-anilinoquinoline-5,8-quinone; and 6-(3-fluoroanilino)quinoline-5,8-quinone.

The following definitions refer to the various terms used throughout this disclosure. The term "$C_1$-$C_6$ alkyl" refers to the straight and branched saturated aliphatic radicals of one to six carbon atoms including methyl, ethyl, propyl, isopropyl, butyl, isobutyl, sec-butyl, tert-butyl, pentyl, isopentyl, sec-pentyl, 1,2-dimethylpropyl, 1,1-dimethylpropyl, neopentyl, hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The term "$C_1$–$C_6$ alkyl" includes within its definition the term "$C_1$–$C_3$ alkyl".

The term "$C_3$–$C_6$ cycloalkyl" refers to the saturated alicyclic rings of three to six carbon atoms, including cyclopropyl, methylcyclopropyl, cyclobutyl, cyclopentyl, cyclohexyl, and the like.

The term "$C_2$–$C_6$ alkenyl" refers to unsaturated aliphatic radicals of two to six carbon atoms including ethylenyl, propenyl, butenyl, pentenyl, hexenyl, and the like.

The term "$C_1$–$C_6$ alkoxy" refers to the alkyl radicals of one to six carbon atoms attached to the remainder of the molecule by oxygen and includes methoxy, ethoxy, propoxy, isopropoxy, butoxy, isobutoxy, sec-butoxy, tert-butoxy, and the like.

The term "$C_1$–$C_3$ alkylthio" refers to the alkyl radicals of one to three carbon atoms attached to the remainder of the molecule by sulfur and includes methylthio, ethylthio, propylthio, and the like.

The term "$C_1$–$C_3$ alkylcarbonyl" refers to the alkyl radical of one to three carbon atoms attached to the remainder of the molecule by a carbonyl group (C=O) and includes methylcarbonyl, ethylcarbonyl, propylcarbonyl, and the like.

The term "$C_1$–$C_6$ alkylamino" refers to the alkyl radical of one to six carbon atoms attached to the remainder of the molecule by an amino group and includes methylamino, ethylamino, propylamino, pentylamino, hexylamino, and the like.

The term "halo" refers to chloro, bromo, fluoro, and iodo.

The preparation of the quinoline-5,8-quinone compounds may follow one of the reaction schemes outlined below:

Scheme A

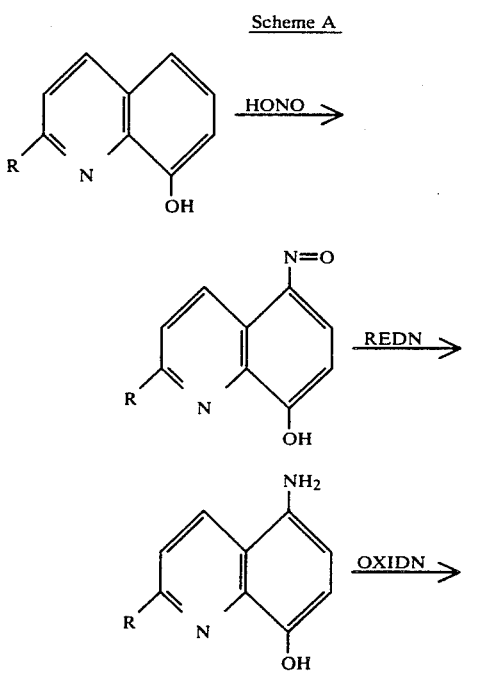

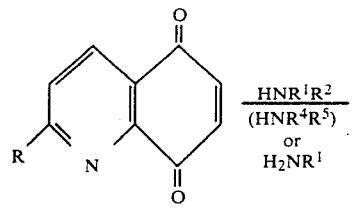

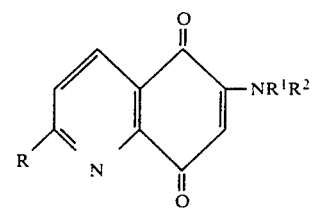

The 8-hydroxyquinoline is reacted with nitrous acid to form 5-nitroso-8-hydroxyquinoline. The nitrous acid is generated in situ by the action of mineral acid, such as hydrochloric, sulfuric, and the like, on sodium nitrite usually under cold temperature conditions.

The nitroso compound is then reduced by hydrogen gas using a metal catalyst, such as Raney nickel, platinum, or palladium; by an acid and an appropriate metal, such as zinc, iron, or tin; by ammonium sulfide; by lithium aluminum hydride; by phenylhydrazine; and the like to form the amino-substituted group. The preferred reduction method is catalytic hydrogenation.

The hydroxy and amino groups are then oxidized by aqueous potassium or sodium dichromate; by chromic acid; by ferric chloride; by chromium (III) oxide in glacial acetic acid or pyridine; by permanganate; and the like, to form quinoline-5,8-quinone. The preferred oxidizing agent is potassium dichromate.

A solution of the amine, usually an aniline, is added to the quinone in the presence of an organic solvent. Such solvents as 1,2-dimethyoxyethane, ethanol, and the like may be employed. The reaction is usually allowed to proceed at room temperature, although elevated temperatures, up to the reflux temperature of the solvent, can be used. Additionally, the introduction of catalytic amounts of cerium chloride is desirable in order to facilitate condensation. The reaction is worked up in the usual manner and the desired product may be purified by conventional means, such as crystallization or chromatography.

Scheme B

-continued
Scheme B

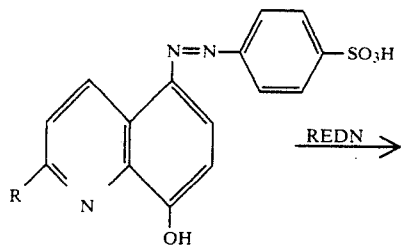

REDN →

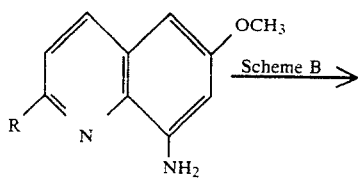

The 8-hydroxyquinoline is coupled with a 4-diazobenzenesulfonic acid salt (chloride, fluoborate) in mildly alkaline solution to form the azo compound. The diazonium salt can be formed by dissolving the appropriate aniline in cold aqueous mineral acid and treating with sodium nitrite.

Sodium dithionite (hyposulfite) is then used to form the 5-amino compound from the azo compound in hot, aqueous, mildly alkaline solution.

Scheme C

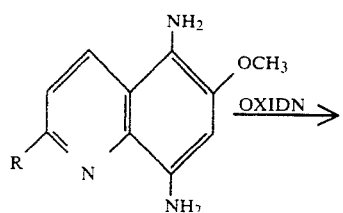

Scheme B →

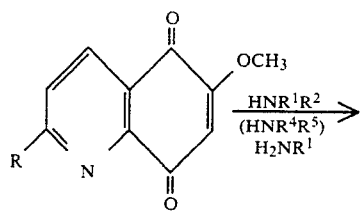

OXIDN →

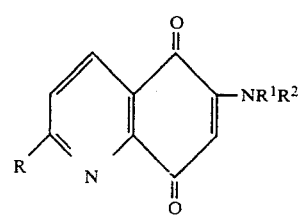

HNR$^1$R$^2$
(HNR$^4$R$^5$)
H$_2$NR$^1$ →

The 5,8-diamino-6-methoxyquinoline is formed from the corresponding 8-amino-6-methoxyquinoline by following Scheme B. Then the diamino compound is oxidized to form the diketone, as described in Scheme A; followed by reaction with a primary or secondary amine to form the claimed compounds. In particular, the 6-methoxyquinoline-5,8-quinone can be reacted with cerous chloride and the amine to form the 6-substituted amino-quinoline-5,8-quinone.

Scheme D

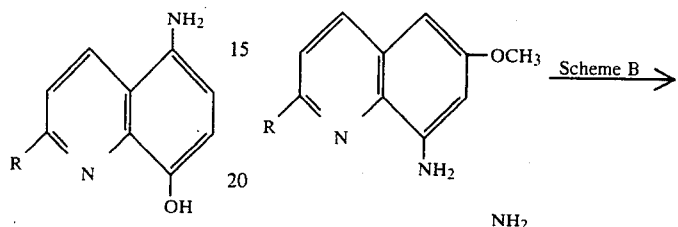

Scheme B →

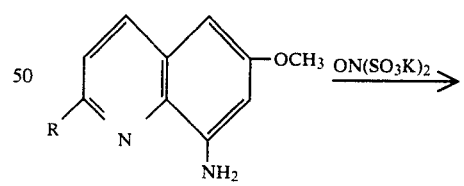

ON(SO$_3$K)$_2$ →

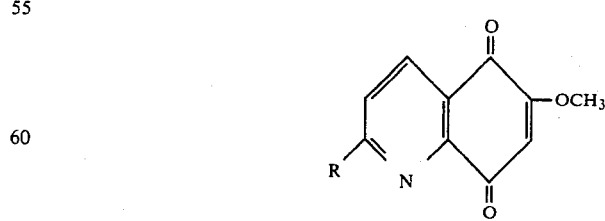

The diamino compound is formed from the corresponding amino compound by following Scheme B. Then the diamino compound is oxidized by Fremy's salt (potassium nitrosodisulfonate) to form the quinoline-5,8-quinone.

Scheme E

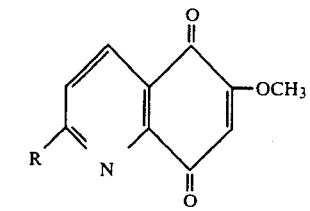

ON(SO$_3$K)$_2$ →

The 8-amino-6-methoxyquinoline can also be oxidized to the diketone, 6-methoxyquinoline-5,8-quinone, using Fremy's salt (potassium nitrosodisulfonate) without going through a diamino intermediate.

Scheme F

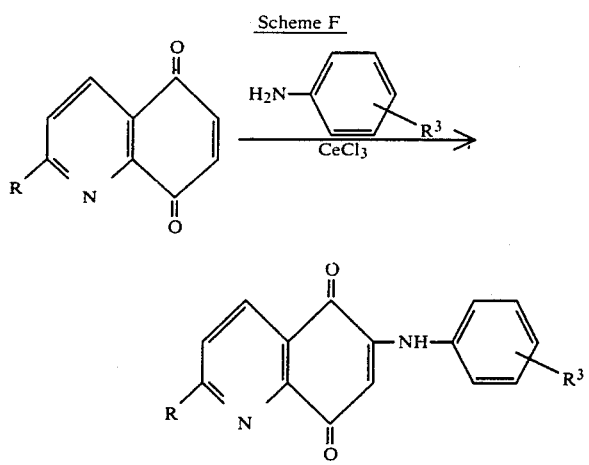

A 6-unsubstituted quinoline-5,8-quinone can also be reacted with cerous chloride and a substituted aniline to form 6-substituted anilinoquinoline-5,8-quinones, as described in the last step of Scheme C.

In particular, the anilinoquinoline-5,8-quinones can be made from the quinoline-5,8-quinone and corresponding aniline in a solvent, such as ethanol, and the like. The anilinoquinoline-5,8-quinone is then crystallized from the solvent, resulting in both the 6- and 7-substituted quinoline-5,8-quinone. Separation of the two isomers can be achieved by routine crystallization, and the desired 6-isomer isolated.

The preparation of some quinoline-5,8-quinones using the above preparation schemes is described in Long, R. and Schofield, K. "Some Properties and Reactions of Quinoline-5:8-quinones", J. Chem. Soc., 3919–3924 (1953); Petrow, V. and Sturgeon, B. "Some Quinoline-5:8-quinones", J. Chem. Soc., 570–574 (1954); Pratt, Y. T. and Drake, N. L. "Quinolinequinones, II. N-Substituted 6-Amino-5,8-quinolinequinones", J. Amer. Chem. Soc., 77, 37–40 (1955); Pratt, Y. T. "Quinolinequinones. VI. Reactions with Aromatic Amines", J. Org. Chem., 27, 3905–3910 (1962); and Pratt, Y. T. and Drake, N. L. "Quinolinequinones, V. 6-Chloro- and 7-Chloro-5,8-quinolinequinones", J. Amer. Chem. Soc., 82, 1155–1161 (1960), which are incorporated by reference.

The preparation of the quinoline quinone compounds of this invention is described in the following examples. The examples are illustrative of the compounds embraced by the invention and of the methods commonly employed in their preparation, but are not to be construed as limiting the invention. All temperatures are in degree Celsius.

EXAMPLE 1

5,8-diamino-6-methoxyquinoline

Thirty-seven and one-half grams of p-sulfonylaniline sodium salt were dissolved in 150 ml of water and the resulting solution was added to 200 ml of 1N hydrochloric acid. Then 150 ml of an aqueous solution of 11.2 g of sodium nitrite were added, forming a reddish solution, which contained p-diazobenzenesulfonic acid.

The reddish diazo solution was added to a solution of 25.0 g of 8-amino-6-methoxyquinoline, 2 L of glacial acetic acid, and 500 ml of saturated aqueous sodium acetate, all of which had been cooled in an ice bath, while the reaction was stirred continuously with the diazo solution being added over about a 2 minute period. The stirring continued for about 1 minute after the diazo solution was added, then the reaction was allowed to sit in the ice bath for about one-half hour. A dark red precipitate was formed, which was filtered, and then washed with water.

The precipitate was then dissolved in a solution of 1 L of water and 50 g of sodium hydroxide and then heated to about 60° for about ten minutes. Slowly, 50 g of sodium dithionite were added with stirring. After the addition, the reaction solution was kept at about 60° for about three hours. An orange precipitate was formed and the reaction was then allowed to cool to room temperature and sodium chloride was added. The orange solid, which was filtered and then dried, weighed 19 g (70% yield). It had a melting point of about 154.5°–155.5° and the mass spectrum showed the expected molecular ion at m/e=189. The pKa was 5.08 using 66% aqueous dimethylformamide solution.

The NMR spectrum (deuterated chloroform) showed the following:

$\delta(ppm)=3.85$: methoxy at 6-position; 6.85: hydrogen at 7-position; 7.3: hydrogen at 3-position; 8.3: hydrogen at 4-position; 8.55: hydrogen at 2-position;

EXAMPLE 2

2-methyl-5-amino-8-hydroxyquinoline

The preparation of 2-methyl-5-amino-8-hydroxyquinoline follows the procedure outlined in Example 1, except 15.9 g of 2-methyl-8-hydroxyquinoline were used as the starting material. The product weighed 4.3 g (24.7% yield) and had a melting point of about 152°–154°. The mass spectrum indicated the expected molecular ion at m/e=174. The pKa was 5.00, using 66% aqueous dimethylformamide solution and the apparent molecular weight was 188. In addition, the IR spectrum showed peaks at 3320 and 3400 cm$^{-1}$.

The NMR spectrum (deuterated chloroform) showed the following:

$\delta(ppm)=2.7$: methyl at 2-position; 6.6: hydrogen at 6-position; 6.9: hydrogen at 7-position; 7.3: hydrogen at 3-position; 8.4: hydrogen at 4-position;

The following elemental analysis was obtained:
Calculated for $C_{10}H_{10}N_2O$:
Theory: C, 68.95; H, 5.79; N, 16.08.
Found: C, 68.57; H, 5.60; N, 15.97.

EXAMPLE 3

6-methoxyquinoline-5,8-quinone

Nineteen grams of 6-methoxy-5,8-diaminoquinoline were dissolved in 450 ml of water and 10 ml of concentrated sulfuric acid. The solution was cooled in an ice bath and then 50 ml of potassium dichromate solution were added. (The dichromate solution was made by dissolving 50 g of potassium dichromate in 500 ml of water.) Forty ml of concentrated sulfuric acid were added, followed by 190 ml of the potassium dichromate solution, then 20 ml of concentrated sulfuric acid, and finally 400 ml of methylene chloride.

The reaction mixture was then stirred slowly and kept at about 25°–30° throughout the reaction. After about 10 minutes, the methylene chloride was separated and 400 ml of fresh methylene chloride were added.

The reaction was continued for another 20 minutes and again the methylene chloride was separated and a further 400 ml of methylene chloride were added. After 40 minutes, the last methylene chloride fraction was separated. All the methylene chloride fractions were then combined and washed with an aqueous sodium chloride solution, then dried with anhydrous sodium sulfate, and evaporated to a tan amorphous powder. The powder was recrystallized in methanol to form yellow needles. The product weighed 4 g (21% yield) and had a melting point of about 246°–249°. The mass spectrum showed the expected molecular ion at m/e=189 and the IR spectrum indicated peaks at 1665 and 1685 cm$^{-1}$.

The following elemental analysis was obtained:
Calculated for $C_{10}H_7NO_3$:
Theory: C, 63.49; H, 3.73; N, 7.40.
Found: C, 63.27; H, 3.93; N, 7.13.

EXAMPLE 4

2-methylquinoline-5,8-quinone

The preparation of 2-methylquinoline-5,8-quinone followed the procedure of Example 3, except that 19 g of 2-methyl-5-amino-8-hydroxyquinoline prepared in Example 2 were used as the starting material. The product weighed 7 g (37% yield) and the mass spectrum indicated the expected ion at m/e=173. The IR spectrum had peaks at 1660 and 1680 cm$^{-1}$.

The NMR spectrum (deuterated chloroform) shows the following:
δ(ppm)=2.8: methyl at 2-position; 7.2: hydrogen at 6- and 7-position; 7.6: hydrogen at 3-position; 8.4: hydrogen at 4-position;

The following elemental analysis was obtained:
Calculated for $C_{10}H_7NO_2$:
Theory: C, 69.36; H, 4.07; N, 8.09.
Found: C, 59.30; H, 4.27; N, 7.27.

EXAMPLE 5 quinoline-5,8-quinone

The preparation of quinoline-5,8-quinone followed by the procedure of Example 3, except 60 g of 5-amino-8-hydroxyquinoline were used as the starting material. The product weighed 30 g (50% yield) and the mass spectrum indicated the expected molecular ion at m/e=159.

The following elemental analysis was obtained:
Calculated for $C_9H_5NO_2$:
Theory: C, 67.93; H, 3.17; N, 8.80.
Found: C, 68.07; H, 3.02; N, 8.85.

EXAMPLE 6

6-methoxyquinoline-5,8-quinone

Eight and seven-tenths grams of 8-amino-6-methoxyquinoline were dissolved in 500 ml of acetone and then 50 ml of a 0.167M of a potassium dihydrophosphate solution were added. Twenty-eight grams of Fremy's salt (potassium nitrosodifulfonate) were slowly added with stirring. The reaction was stirred at room temperature for several hours until the color changed from purple to red.

The acetone was removed from the reaction mixture in vacuo, then the resulting solution was extracted three times with chloroform. The chloroform extracts were combined, then dried with sodium sulfate and evaporated in vacuo to give a tan amorphous powder weighing 1 g (11% yield). The mass spectrum showed the expected molecular ion at m/e=189.

EXAMPLE 7

6-anilinoquinoline-5,8-quinone

Six grams of 6-methoxyquinoline-5,8-quinone were dissolved in 500 ml of absolute ethanol and 9 g of cerium chloride were added. After the reaction was stirred, 3.3 g of aniline were added. The reaction mixture was refluxed for several hours, then it was stirred overnight at room temperature. The ethanol was evaporated to dryness and partitioned between chloroform and an aqueous sodium chloride solution. The chloroform layer was washed with an aqueous sodium chloride solution, dried with sodium sulfate, and then evaporated. The product was crystallized from absolute ethanol and weighed 3 g (16% yield). It had a melting point of about 182°–184° and the mass spectrum indicated the expected molecular ion at m/e=250.

The following elemental analysis was obtained:
Calculated for $C_{15}H_{10}N_2O_2$:
Theory: C, 71.99; H, 4.03; N, 11.19.
Found: C, 71.73; H, 3.76; N, 11.37.

EXAMPLE 8

6-(4-methoxyanilino)quinoline-5,8-quinone

The preparation of 6-(4-methoxyanilino)quinoline-5,8-quinone followed the procedure in Example 7, except that 3.8 g of 6-methoxyquinoline-5,8-quinone and 2.5 g of 4-methoxyaniline were used as the starting materials. The product had a melting point of about 212°–213°. The mass spectrum indicated the expected molecular ion at m/e=280.

The NMR spectrum (deuterated chloroform) showed the following:
(ppm)=3.8: methoxy at 4-position of aniline ring; 6.4: hydrogen at 7-position; 6.9: hydrogen at 2-position of aniline ring; 7.2: hydrogen at 3-position of aniline ring; 7.5: hydrogen at 4-position; 8.4: hydrogen at 3-position; 8.8: hydrogen at 2-position.

The following elemental analysis was obtained:
Calculated for $C_{16}H_{12}N_2O_3$:
Theory: C, 68.56; H, 4.32; N, 9.99.
Found: C, 68.79; H, 4.54; N, 9.70.

EXAMPLE 9

6-(4-nitroanilino)quinoline-5,8-quinone

The preparation of 6-(4-nitroanilino)quinoline-5,8-quinone followed the procedure outlined in Example 7.

The product weighed 0.1 g (3% yield) and the mass spectrum indicated the expected molecular ion at m/e=295.

The following elemental analysis was obtained:
Calculated for $C_{15}H_9N_3O_3$:
Theory: C, 61.02; H, 3.07; N, 14.23.
Found: C, 60.85; H, 3.36; N, 13.96.

EXAMPLE 10

6-anilinoquinoline-5,8-quinone

Twenty and one-half grams of quinoline-5,8-quinone were dissolved in 500 ml of absolute ethanol, then 13 g of aniline were added, followed by the addition of 32 g of cerium chloride. This reaction mixture was refluxed overnight. The resulting mixture had a brown-blue color and was stirred and then left to cool to room temperature for about 26 hours.

Afterward the mixture was evaporated to dryness, boiled in ethyl acetate with some ethanol, and then washed with an aqueous sodium chloride solution. Upon drying with sodium sulfate, the reaction mixture was evaporated to dryness in vacuo. The product was crystallized from absolute ethanol and weighed 11 g (34% yield).

The following elemental analysis was obtained:
Calculated for $C_{15}H_{10}N_2O_2$:
Theory: C, 71.99; H, 4.03; N, 11.19.
Found: C, 71.96; H, 4.03; N, 10.98.

The following compounds were prepared as in Example 10 and are shown in Table I:

10.0. Poorly perfused and bloody areas were discarded. Normal lung was cut into 1 mm cubes with a McIlwain tissue chopper, washed with Krebs' solution and divided into 400 mg aliquots. The fragmented tissue was then incubated at 37° C. for 15 minutes in Krebs' solution containing indomethacin to optimize SRS-A release and an appropriate concentration of experimental drug. Antigen (ovalbumin) was then added to make a final concentration of $1 \times 10^{-5}$ g/ml. Fifteen minutes later, the incubation medium was decanted and centrifuged at 3,000 g at 4° C. for 5 minutes. The supernatant

TABLE I

| Example No. | Compound | Mass Spectrum m/e = | Elemental Analysis Theory | | | Found | | |
|---|---|---|---|---|---|---|---|---|
| | | | C | H | N | C | H | N |
| 11 | 2-methyl-6-anilinoquinoline-5,8-quinone | 264 | 72.72 | 4.58 | 10.60 | 72.94 | 4.82 | 10.37 |
| 12 | 6-(1-amino-5,6,7,8-tetrahydronaphthalene)quinoline-5,8-quinone | 304 | 74.98 | 5.30 | 9.20 | 75.12 | 5.62 | 8.92 |
| 13 | 6-(4-hydroxyanilino)quinoline-5,8-quinone | 266 | 67.67 | 3.79 | 10.52 | 67.09 | 4.22 | 10.41 |
| 14 | 6-cyclohexylaminoquinoline-5,8-quinone | 256 | 70.29 | 6.29 | 10.93 | 70.06 | 6.12 | 10.69 |
| 15 | 6-(N—ethylanilino)quinoline-5,8-quinone | 278 | 73.37 | 5.07 | 10.07 | 73.67 | 4.78 | 9.96 |
| 16 | 6-(flouroanilino)quinoline-5,8-quinone | 268 | 67.16 | 3.38 | 10.44 | 66.95 | 3.66 | 10.14 |
| 17 | 6-(2-flouroanilino)quinoline-5,8-quinone | 268 & 162 | 67.16 | 3.38 | 10.44 | 66.44 | 3.59 | 10.12 |
| 18 | 6-dimethylaminoethylamino-quinoline-5,8-quinone | 245 | 63.66 | 6.16 | 17.13 | 63.46 | 6.09 | 16.91 |
| 19 | 6-(3-flouroanilino)quinoline-5,8-quinone | 268 | 67.16 | 3.38 | 10.44 | 66.90 | 3.20 | 10.14 |
| 20 | 6-(3-methylanilino)quinoline-5,8-quinone | 264 | 72.72 | 4.58 | 10.60 | 72.85 | 4.81 | 10.47 |
| 21 | 6-(3-methoxyanilino)quinoline-5,8-quinone | 280 | 68.56 | 4.32 | 9.99 | 69.22 | 4.56 | 10.26 |
| 22 | 6-(3-chloroanilino)quinoline-5,8-quinone | 284 & 286 | 63.28 | 3.19 | 9.84 | 62.95 | 3.22 | 9.55 |
| 23 | 6-(3-bromoanilino)quinoline-5,8-quinone | 328 & 330 | 54.74 | 2.76 | 8.51 | 54.92 | 2.78 | 8.50 |
| 24 | 6-(3-triflouromethylanilino)-quinoline-5,8-quinone | 318 | 60.38 | 2.85 | 8.80 | 60.38 | 2.69 | 8.52 |
| 25 | 6-(3-acetylanilino)quinoline-5,8-quinone | 292 | 69.86 | 4.14 | 9.58 | 70.08 | 4.25 | 9.32 |

The compounds of formula (II) are useful in treating any clinical condition characterized by excessive release of slow-reacting substances of anaphylaxis (leukotrienes; SRS-A), which include immediate-type hypersensitivity reactions, such as asthma. Evidence obtained over the past few years has shown the presence of leukotrienes in sputum of patients with chronic bronchitis (Turnbull et al., Lancet II: 526, 1977) or cystic fibrosis (Cromwell et al. Lancet II: 164, 1981), suggesting a role for these substances in the pathology of these diseases. Therefore, the compounds described in this invention also should alleviate some of the symptoms of chronic bronchitis and cystic fibrosis by virtue of their ability to inhibit the release of leukotrienes.

The following test procedure and results demonstrate the utility of the compounds in inhibiting the release of leukotrienes. Male, Hartley guinea pigs, usually 1-2 weeks old were sensitized with respect to ovalbumin by intraperitoneal administration of 0.15 ml hyperimmune serum obtained from guinea pigs actively sensitized against ovalbumin. After 2 days or more, the animals were decapitated, lungs were excised and perfused through the pulmonary artery with Krebs' bicarbonate solution of the following composition in mmoles/liter: KCl, 4.6; $CaCl_2.2H_2O$, 1.8; $KH_2PO_4$, 1.2; $MgSO_4.7H_2O$, 1.2; NaCl, 118.2; $NaHCO_3$, 24.8; and dextrose, solution was collected and assayed for SRS-A using a computerized bioassay that employs the isolated guinea pig ileum (Fleisch et al., J. Pharmacol. Exp. Ther., 209, 238-243, 1979, which is incorporated by reference). Release of SRS-A in the presence of an experimental drug was compared to a control sample and the results expressed as percent inhibition of SRS-A release. These results are shown in Table II:

TABLE II

| | Inhibition of SRS-A Release | | | |
|---|---|---|---|---|
| | Percent Inhibition in M Concentration | | | |
| Compound of Example No. | $3 \times 10^{-5}$ | $1 \times 10^{-5}$ | $3 \times 10^{-6}$ | $1 \times 10^{-6}$ |
| 7,10 | 86 | 79 | 54 | 28 |
| 8 | NT* | 32 | NT | NT |
| 9 | NT | 41 | NT | NT |
| 11 | NT | 55 | NT | NT |
| 12 | NT | 23 | NT | NT |
| 13 | NT | 58 | NT | NT |
| 14 | NT | 53 | NT | 0 |
| 15 | NT | 53 | NT | NT |
| 16 | NT | 39 | NT | NT |
| 17 | NT | 71 | NT | 0 |
| 18 | NT | 40 | NT | NT |
| 19 | 94 | 76 | 42,80 | 13 |

TABLE II-continued
Inhibition of SRS-A Release

| | Percent Inhibition in M Concentration | | | |
|---|---|---|---|---|
| | $3 \times 10^{-5}$ | $1 \times 10^{-5}$ | $3 \times 10^{-6}$ | $1 \times 10^{-6}$ |
| 20 | NT | 69 | NT | NT |
| 21 | NT | 72 | NT | NT |
| 22 | NT | 71 | NT | NT |
| 23 | NT | 45 | NT | NT |
| 24 | NT | 53 | NT | NT |
| 25 | NT | NT | 36 | NT |
| Compound | | | | |
| 6-(2-methylanilino)-quinoline-5,8-quinone | 80 | NT | 17 | NT |
| 6-(2-methoxyanilino)-quinoline-5,8-quinone | 38 | NT | 0 | NT |
| 6-(4-methoxyanilino)-quinoline-5,8-quinone | NT | 32 | NT | NT |
| 6-(2-chloroanilino)-quinoline-5,8-quinone | 78 | NT | 23 | 24 |
| 6-(4-chloroanilino)-quinoline-5,8-quinone | 68 | 23 | NT | NT |
| 6-(2-trifluoromethyl-anilino)quinoline-5,8-quinone | NT | 52 | NT | NT |
| 6-(3-methylthioanilino)-quinoline-5,8-quinone | 55 | NT | 16 | NT |
| 6-(N—methylanilino)-quinoline-5,8-quinone | NT | 80 | 27 | 16 |
| 6-(N—propylanilino)-quinoline-5,8-quinone | 39 | 28 | NT | NT |
| 6-[N—(2-propenyl)-anilino]quinoline-5,8-quinone | NT | 41 | NT | NT |
| 6-methylaminoquinoline-5,8-quinone | 51 | 28 | NT | NT |
| 6-isopropylamino-quinoline-5,8-quinone | 28 | NT | NT | NT |
| 6-cyclopropylamino-quinoline-5,8-quinone | 48 | NT | NT | NT |
| 6-(2-propenyl)amino-quinoline-5,8-quinone | NT | 53 | NT | NT |
| 6-methylpropylamino-quinoline-5,8-quinone | 61 | NT | NT | NT |
| 6-piperidinylquinoline-5,8-quinone | NT | 68 | NT | NT |
| 6-morpholinylquinoline-5,8-quinone | 63 | 28 | NT | NT |

*NT = Not Tested

The compounds or formulations of the present invention may be administered by the oral and rectal routes, topically, parenterally, e.g. by injection and by continuous or discontinuous intra-arterial infusion. These formulations can be in the form of, for example, tablets, lozenges, sub-lingual tablets, sachets, cachets, elixirs, suspensions, aerosols and ointments, containing an appropriate amount of the active compound in a suitable base. In addition, they can be soft and hard gelatin capsules, suppositories, injection solutions and suspensions in physiologically acceptable media, or sterile packaged powders adsorbed onto a support material for making injection solutions. Advantageously for this purpose, compositions may be provided in dosage unit form, preferably each dosage unit containing from 5 to 500 mg (from 5.0 to 50 mg in the case of parenteral administration, from 5.0 to 50 mg in the case of inhalation and from 25 to 500 mg in the case of oral or rectal administration) of a compound of formula (I) or (II). Dosages of from 0.5 to 300 mg/kg per day, preferably 0.5 to 20 mg/kg of active ingredient may be administered, although it will, of course, readily be understood that the amount of the compound or compounds actually to be administered will be determined by a physician, in the light of all the relevant circumstances, including the condition to be treated, the choice of compound to be administered, and the choice of route of administration. Therefore, the above preferred dosage range is not intended to limit the scope of the present invention.

In this specification, the expression "dosage unit form" is used as meaning a physically discrete unit containing an individual quantity of the active ingredient, generally in admixture with a pharmaceutical diluent therefore, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) or (II) mixed with a carrier; or diluted by a carrier; or enclosed or encapsulated by an ingestible carrier in the form of a capsule, sachet, cachet, paper or other container; or by a disposable container such as an ampoule. A carrier or diluent may be a solid, semi-solid, or liquid material, which serves as a vehicle, excipient, or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup U.S.P., methyl cellulose, polyoxyethylene sorbitan monolaurate, ethyl lactate, methyl and propyl hydroxybenzoate, sorbitan trioleate, sorbitan sesquioleate, and oleyl alcohol. Propellants can be trichloromonofluoromethane, dichlorodifluoromethane, and dichlorotetrafluoroethane, and the like. In the case of tablets, a lubricant may be incorporated to prevent sticking and binding of the powdered ingredients in the dies and on the punch of the tableting machine. For such purpose there may be employed, for instance, aluminium, magnesium, or calcium stearates; talc; or mineral oil.

Preferred pharmaceutical forms of the present invention are capsules, tablets, suppositories, suspensions, aerosols, injectible solutions, creams, and ointments. The most preferred forms are those used for inhalation application, such as suspensions, aerosols, and the like. Especially preferred is an aerosol formulation for inhalation application.

We claim:

1. A compound of formula (I):

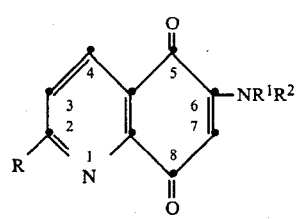

wherein

R is hydrogen or $C_1$–$C_3$ alkyl;

$R^1$ and $R^2$ are hydrogen; $C_3$–$C_6$ cycloalkyl; $C_2$–$C_6$ alkenyl; tetrahydronaphthyl; together with the nitrogen atom form a morpholine ring; or phenyl substituted by R³; and R³ is hydrogen; C₁-C₆ alkyl, except ortho ethyl, and para methyl; C₂-C₆ alkenyl; C₁-C₆ alkoxy; halo, except para chloro; trifluoromethyl, except in the para position; nitro; hydroxy; C₁-C₃ alkylthio; or C₁-C₃ alkylcarbonyl;

providing that R¹ and R² are not both hydrogen or phenyl, and further providing that R¹ is not phenyl when R and R² are hydrogen.

2. The compound of claim 1 wherein R¹ is phenyl substituted by R³ and R² is hydrogen.

3. The compound of claim 2 wherein R³ is halo or methyl.

4. The compound of claim 3 wherein is 6-(3-fluoroanilino)quinoline-5,8-quinone.

5. A method of treating an animal, including a human, suffering from or susceptible to any condition characterized by an excessive release of leukotrienes, which comprises administering to said animal a therapeutically-effective amount of a compound of formula (II):

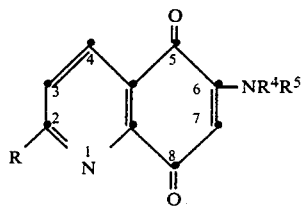

wherein
R is hydrogen or C₁-C₃ alkyl;

R⁴ and R⁵ are hydrogen; C₁-C₆ alkyl; C₃-C₆ cycloalkyl; C₂-C₆ alkenyl; di(C₁-C₆ alkyl)amino C₁-C₆ alkyl; tetrahydronaphthyl; together with the nitrogen atom form a morpholine ring; or phenyl substituted by R³; and R³ is hydrogen; C₁-C₆ alkyl, except ortho ethyl; C₂-C₆ alkenyl; C₁-C₆ alkoxy; halo; trifluoromethyl, except in the para position; nitro; hydroxy; C₁-C₃ alkylthio; or C₁-C₃ alkylcarbonyl.

6. The method of claim 5 wherein R⁴ is phenyl substituted by R³ and R⁵ is hydrogen.

7. The method of claim 6 wherein R³ is hydrogen, halo, or methyl.

8. The method of claim 7 in which the compound is 6-(3-fluoroanilino)quinoline-5,8-quinone.

9. The method of claim 7 in which the compound is 6-anilinoquinoline-5,8-quinone.

10. A method of treating asthma, which comprises administering a therapeutically-effective amount of a compound of formula (II):

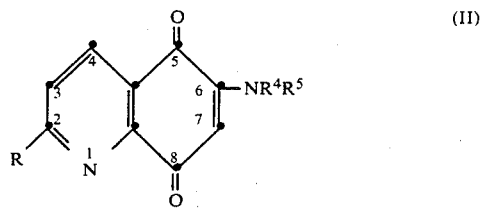

wherein
R is hydrogen or C₁-C₃ alkyl;

R⁴ and R⁵ are hydrogen; C₁-C₆ alkyl; C₃-C₆ cycloalkyl; C₂-C₆ alkenyl; di(C₁-C₆ alkyl)amino C₁-C₆ alkyl; tetrahydronaphthyl; together with the nitrogen atom form a morpholine ring; or phenyl substituted by R³; and R³ is hydrogen; C₁-C₆ alkyl, except ortho ethyl; C₂-C₆ alkenyl; C₁-C₆ alkoxy; halo; trifluoromethyl, except in the para position; nitro; hydroxy; C₁-C₃ alkylthio; or C₁-C₃ alkylcarbonyl.

11. The method of claim 10 wherein R⁴ is phenyl substituted by R³ and R⁵ is hydrogen.

12. The method of claim 11 wherein R³ is hydrogen, halo, or methyl.

13. The method of claim 12 in which the compound is 6-(3-fluoroanilino)quinoline-5,8-quinone.

14. The method of claim 12 in which the compound is 6-anilinoquinoline-5,8-quinone.

15. A pharmaceutical formulation useful for the treatment of asthma which comprises as the active ingredient a therapeutically-effective amount of a compound of claim 1 associated with a pharmaceutically-acceptable carrier therefor.

16. The formulation of claim 15 in which the compound is 6-(3-fluoroaniline)quinoline-5,8-quinone.

17. The formulation of claim 15 which is formulated for inhalation.

18. The formulation of claim 17 which is formulated as an aerosol.

19. The formulation of claim 18 in which the compound is 6-(3-fluoroaniline)quinoline-5,8-quinone.

* * * * *